US007476248B2

(12) United States Patent (10) Patent No.: US 7,476,248 B2
Harris et al. (45) Date of Patent: Jan. 13, 2009

(54) METHOD OF CALCULATING THE REQUIRED LENS POWER FOR AN OPTHALMIC IMPLANT

(75) Inventors: Blake Harris, Mansfield, TX (US); James Hoffman, Garland, TX (US); Xin Hong, Arlington, TX (US); Xiaoxiao Zhang, Fort Worth, TX (US); Warren E. Hill, Mesa, AZ (US)

(73) Assignee: Alcon, Inc., Hunenberg (CH)

( * ) Notice: Subject to any disclaimer, the term of this patent is extended or adjusted under 35 U.S.C. 154(b) by 366 days.

(21) Appl. No.: 10/819,020

(22) Filed: Apr. 6, 2004

(65) Prior Publication Data

US 2005/0225721 A1 Oct. 13, 2005

(51) Int. Cl.
*A61F 2/14* (2006.01)
*A61F 2/16* (2006.01)
(52) U.S. Cl. .................................. 623/5.11; 623/6.11
(58) Field of Classification Search ................ 623/6.11, 623/6.23, 6.24, 5.11
See application file for complete search history.

(56) References Cited

U.S. PATENT DOCUMENTS

| | | | | |
|---|---|---|---|---|
| 3,880,502 | A * | 4/1975 | Humphrey | 351/246 |
| 4,859,261 | A * | 8/1989 | Ace | 156/102 |
| 4,964,717 | A * | 10/1990 | Koester | 351/219 |
| 5,092,880 | A | 3/1992 | Ohmi | |
| 5,282,852 | A * | 2/1994 | Capetan et al. | 623/6.11 |
| 5,512,965 | A * | 4/1996 | Snook | 351/205 |
| 5,514,124 | A * | 5/1996 | Alpins | 606/4 |
| 5,709,218 | A | 1/1998 | Holladay et al. | |
| 5,728,155 | A * | 3/1998 | Anello et al. | 623/6.47 |
| 5,740,815 | A * | 4/1998 | Alpins | 128/897 |
| 5,968,095 | A * | 10/1999 | Norrby | 128/898 |
| 6,120,148 | A * | 9/2000 | Fiala et al. | 351/161 |
| 6,467,906 | B1 * | 10/2002 | Alpins | 351/212 |
| 6,505,936 | B1 | 1/2003 | Holladay et al. | |
| 6,634,751 | B2 * | 10/2003 | Turner et al. | 351/212 |
| 6,663,240 | B2 * | 12/2003 | Patel | 351/200 |
| 7,044,604 | B1 * | 5/2006 | Arrowsmith | 351/246 |
| 7,241,311 | B2 * | 7/2007 | Norrby et al. | 623/6.11 |
| 2002/0105617 | A1 * | 8/2002 | Norrby et al. | 351/177 |

OTHER PUBLICATIONS

Thibos, et al. "Power Vectors: An Application of Fourier Analysis to the Description and Statistical Analysis of Refractive Error," Optometry and Vision Science, Jun. 1997, vol. 74, No. 6.
Holladay, et al "Calculating the surgically induced refractive change following ocular surgery," Journal Cataract Refractive Surgery, Sep. 1992, vol. 18, p. 429.
Thibos, et al "Power vector analysis of the optical outcome of refractive surgery," Journal Cataract Refractive Surgery, Jan. 2001, vol. 27, p. 80.
Lang. Presentation to ANSI members, "Toric IOL Inspection," ISO/TC 172/SC 7WG 7 N 414 Jun. 16, 2003.

\* cited by examiner

*Primary Examiner*—Paul Prebilic
(74) *Attorney, Agent, or Firm*—Jonathan E. Prejean

(57) ABSTRACT

A method for calculating the required cylindrical power of a toric implant by using both the measured pre-operative corneal/ocular astigmatism and the predicted surgically-induced astigmatism. The post-operative corneal/ocular astigmatism is predicted using power vector analysis of the surgical technique employed by the surgeon. Such a method provides a more accurate method of calculating the required spherocylindrical refractive power of the implant. The method can be implemented manually, but preferably is automated by implementation on a computer through appropriate software.

3 Claims, 2 Drawing Sheets

METHOD OF CALCULATING THE REQUIRED LENS POWER FOR AN OPTHALMIC IMPLANT

BACKGROUND OF THE INVENTION

This invention relates generally to the field of ophthalmic lenses and, more particularly, to toric intraocular lenses (e.g. pseudophakic IOL, AC phakic IOL, PC phakic IOL, Iris-fixed IOL and etc.).

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In the normal, healthy eye, sharp images are formed on the retina (emmetropia). In many eyes, images are either formed in front of the retina because the eye is abnormally long (axial myopia), or formed in back of the retina because the eye is abnormally short (axial hyperopia). The cornea and crystalline lens also may be non-spherical and regular but asymmetric or toric, resulting in an uncompensated cylindrical refractive error referred to as corneal and lenticular astigmatisms, which in combination give ocular astigmatism. Finally, if a surgical procedure is performed on the eye, the procedure itself can induce corneal astigmatism.

These refractive errors can all be corrected by the use of a refractive implant, when the natural lens is left in place, or by an intraocular lens (IOL) that is used to replace the natural lens. With respect to a toric implant, the magnitude of the cylindrical power of the implant and the exact alignment of the implant with the naturally occurring or induced asymmetry of the cornea/eye is necessary in order to correct the regular astigmatism of the cornea/eye. The importance of the alignment of the axis of the implant with that of the cornea/eye is important because even with matching magnitudes of cylinder, any misalignment of the axis results in unintended residual refractive errors with both sphere and cylinder. Thus, misalignment of the axis of cylinder of the implant with that of the cornea/eye is detrimental to the overall goal of optimum retinal image formation. The criticality of the needed alignment depends upon the magnitude of corneal/ocular cylinder, especially for large magnitude of corneal/ocular cylinder.

One prior art method for predicting the required spherical IOL power based on surgical techniques is disclosed in U.S. Pat. No. 5,709,218 (Holladay, et al.). This method, however, does not use power vector analysis to determine the correct power or orientation of a toric implant. There are various mathematical models available to assess surgically induced astigmatism. Authors such as Thibos, Holladay, Horner, Cravy and Koch have published papers on the use of power vector analysis to evaluate induced refractive error by Lasik surgery. The above methods provided the assessments for correction effectiveness. They, however, failed to provide a direct guidance for surgeons in terms of how to do surgery correctly to optimal refractive outcomes. In addition, these models do not account for the location of the lens within the eye.

Accordingly, a need continues to exist for a method of calculating the predicted post-operative refractive error in an eye that takes into account both naturally occurring and surgically induced astigmatic errors.

BRIEF SUMMARY OF THE INVENTION

The present invention improves upon the prior art by providing a method for calculating the required power of a toric implant by using both the measured pre-operative corneal/ocular astigmatism and the predicted surgically-induced astigmatism. The surgically-induced astigmatism is predicted using power vector analysis of the surgical technique employed by the surgeon. Such a method provides a more accurate method of calculating the required post-operative refractive power of the implant. The method can be implemented manually, but preferably is automated by implementation on a computer through appropriate software.

Accordingly, one objective of the present invention is to provide a method for calculating the required power of a toric implant by using both the measured pre-operative corneal/ocular astigmatism and the predicted surgically-induced astigmatism.

Another objective of the present invention is to provide a method for calculating the required power of a toric implant using power vector analysis of the surgical technique employed by the surgeon.

Still another objective of the present invention is to provide a more accurate method of calculating the required post-operative refractive power of the implant.

These and other advantages and objectives of the present invention will become apparent from the detailed description and claims that follow.

DETAILED DESCRIPTION OF THE INVENTION

Figure 1:
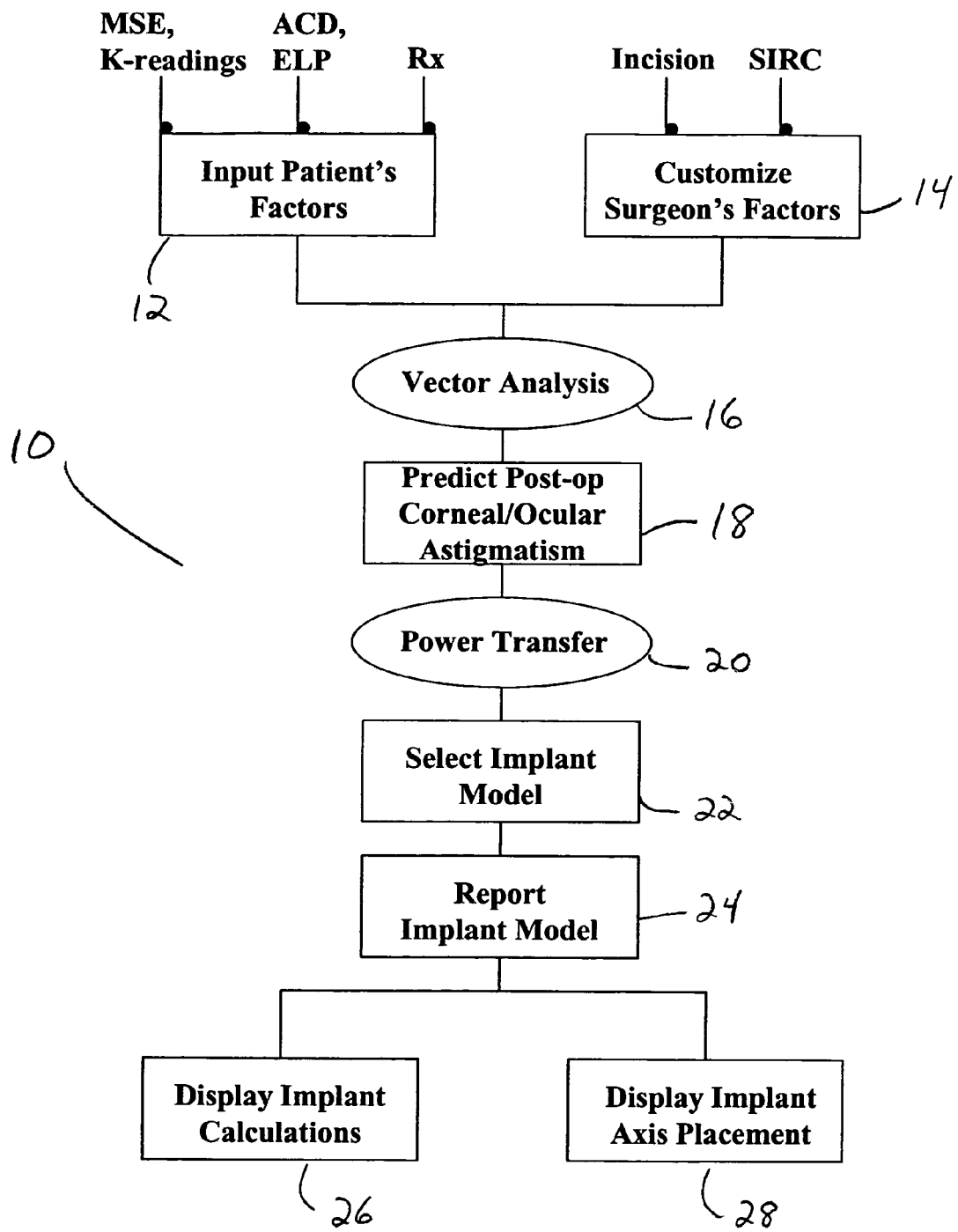
FIG. 1 is a flow chart indicating the steps of the method of the present invention.

Method 10 of the present invention generally includes determining the magnitude of the astigmatic error of a patient based on patient factors and surgeon factors. Patient factors (12) include (i) the mean sphere equivalent (MSE) of the implant, (ii) the K-reading for the steepest meridian ($K_1$) and axis ($A_1$) and the K-reading for the flattest meridian ($K_2$) and axis ($A_2$), (iii) anterior chamber depth (ACD) or effective lens position (ELP) and (iv) the manifest refraction of the whole eye (in the case of calculating ocular astigmatism). Surgeon factors (14) include incision size and location (incision) and the surgically induced refractive change (SIRC) typical for the individual surgeon. Both patient factors 12 and surgeon factors 14 are analyzed at step 16 using a power vector analysis. Step 16 may use any of a variety of mathematical formulas well-known in the art, one suitable formula will now be discussed. The sphero-cylindrical prescription (S, C and α), either in optometric convention (−cyl format) or in ophthalmologic convention (+cyl format), can be described by M, $J_0$ and $J_{45}$ as following:

$$M = S + \frac{C}{2}; \tag{1}$$

-continued $$J_0 = -\frac{C}{2}\cos(2\alpha);$$

$$J_{45} = -\frac{C}{2}\sin(2\alpha);$$

$$B = \sqrt{M^2 + J_0^2 + J_{45}^2}$$

where B is called the blur strength. It's the equivalent dioptric defocus at the plane of the least confusion.

The refractive error in power vector format can be converted back to the sphero-cylindrical format. Since the optometric (−cyl format) and ophthalmologic (+cyl format) conventions are easily interchangeable, the conversion from M, $J_0$ and $J_{45}$ to the optometric (−cyl format) convention is presented in equation (2).

$$C = -2\sqrt{J_0^2 + J_{45}^2};$$

$$S = M - \frac{C}{2};$$

$$\alpha = \begin{cases} \frac{1}{2}\tan^{-1}\left(\frac{J_{45}}{J_0}\right) & J_0 \geq 0 \ \& \ \tan^{-1}\left(\frac{J_{45}}{J_0}\right) \geq 0 \\ \frac{1}{2}\tan^{-1}\left(\frac{J_{45}}{J_0}\right) + 180° & J_0 \geq 0 \ \& \ \tan^{-1}\left(\frac{J_{45}}{J_0}\right) < 0 \\ \frac{1}{2}\tan^{-1}\left(\frac{J_{45}}{J_0}\right) + 90° & J_0 < 0 \ \& \ \tan^{-1}\left(\frac{J_{45}}{J_0}\right) \geq 0 \\ \frac{1}{2}\tan^{-1}\left(\frac{J_{45}}{J_0}\right) + 90° & J_0 < 0 \ \& \ \tan^{-1}\left(\frac{J_{45}}{J_0}\right) < 0 \end{cases}$$

(2)

The cylinder axis in clinical prescription is usually falling between 0° and 180°. To get the axis within the legitimate range, four different conditions can be encountered, shown in equation (2).

The current corneal incision procedure of cataract surgery causes both the flattening and the steepening of the corneal surface at meridians associated with the incision locations. This creates a measurable cylinder power change and cylindrical axis shift in post-operative refraction. Surgically induced astigmatic change should be taken into account in predicting the post-operative astigmatism and then it is possible to use a toric implant to neutralize the astigmatism in the whole eye. Using the equation (1), the corneal refractive error, $S_{Cornea}$, $C_{Cornea}$ and $\alpha_{Cornea}$, and the surgically induced refractive change (SIRC), $S_{SIRC}'$, $C_{SIRC}'$ and $\alpha_{SIRC}'$, can be converted into power vectors. For simplicity, the power vector of corneal refractive error is denoted as (M, $J_0$, $J_{45}$) and the power vector of SIRC is denoted as (M', $J_0'$, $J_{45}'$). The power vector for the predicted post-operative corneal refractive error is the sum of cornea and SIRC power vectors.

$$Rx_{Cornea}=(M, J_0, J_{45}); Rx_{SIRC}'=(M', J_0', J_{45}')$$

$$Rx_{Xcyl}=Rx_{Cornea}+Rx_{SIRC}'=(M+M', J_0+J_0', J_{45}+J_{45}') \quad (3)$$

In the case of the whole eye, the refractive error of the whole eye is $S_{Eye}$, $C_{Eye}$ and $\alpha_{Eye}$ and therefore the equations can be rewritten as:

$$Rx_{Eye}=(M, J_0, J_{45}); Rx_{SIRC}'=(M', J_0', J_{45}')$$

$$Rx_{Xcyl}=Rx_{Eye}+Rx_{SIRC}'=(M+M', J_0+J_0', J_{45}+J_{45}')$$

The predicted post-operative corneal/ocular vector can be converted to conventional sphero-cylindrical format by using equation (2). The conversion results are labeled as $S_{Xcyl}$, $C_{Xcyl}$ and $\alpha_{Xcyl}$, for the reason that they are the results of cross-cylinder calculation.

For toric implant selection, the focus will be on the cylindrical components $C_{Xcyl}$ and $\alpha_{Xcyl}$. At the corneal plane, a toric correction with $C_{Xcyl}$ and $\alpha_{Xcyl}$ are required. However, the toric correction needed at the implant plane is different from that at corneal plane due to the power transfer property from the corneal plane to the implant plane. The toric implant has the cylinder power and cylindrical axis described by equation (4).

$$C_{Implant}=CF*C_{Xcyl}$$

$$\alpha_{Implant}=\alpha_{Xcyl} \quad (4)$$

where CF is conversion factor between the corneal plane and the implant plane. From the calculated values $C_{Implant}$ and $\alpha_{Implant}$, the appropriate toric implant model can be selected and the selected implant will be placed at the meridian indicated by $\alpha_{Implant}$. The vector analysis contemplated in step 16 results in calculated post-operative corneal/ocular astigmatism 18, which takes into account both patient factors 12 and surgeon factors 14. If the implant is an intraocular lens (IOL), the predicted cylindrical error calculated at step 18 at the corneal plane is translated into a required cylindrical error at the implant plane at step 20.

In the following discussion, the general rule is that the power of optical component is denoted by "P" and the vergence by "L". We define $P_{cornea}$ as the power of cornea at certain meridian, $P_{Implant}$ as the power of the implant, $P_{Implant}'$ as the equivalent power of the implant at the corneal plane, $L_{cornea}$ as the vergence immediately after the corneal plane, $L_{Implant}$ as the vergence at the first principal plane of the implant, $L_{Implant}'$ as the vergence at the second principal plane of the implant, n as the refractive index of aqueous humor, and d is the distance between the cornea and the first principal plane of the implant.

Generally, the $L_{cornea}$ is equal to the sum of vergence of spectacle correction at the corneal plane and the power of the cornea.

$$L_{cornea}=L_{Rx}+P_{cornea} \quad (5)$$

where the $L_{Rx}$ is the vergence of spectacle correction at the corneal plane. For emmetropic eye after cataract surgery, the $L_{Rx}$ is equal to zero. In the following discussion, if not specifically mentioned, we consider the $L_{cornea}$ the same as the $P_{cornea}$.

Figure 2:
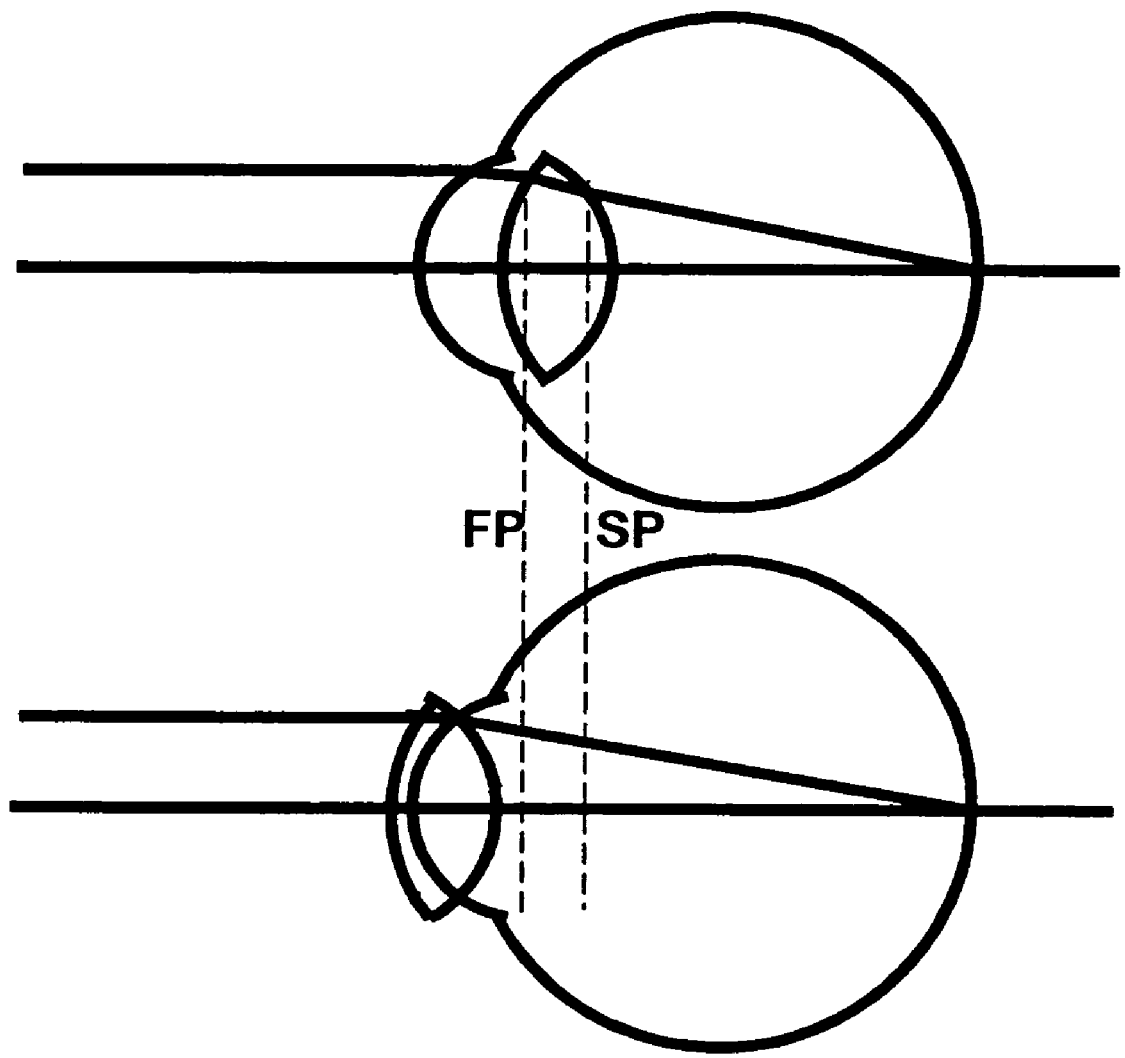
FIG. 2 is a schematic illustration of an eye with an intraocular lens physically placed at the implant plane and virtually placed at the corneal plane.

As shown in FIG. 2, in the top illustration, the implant is physically placed at the implant plane. In the bottom illustration, the implant is virtually placed at the corneal plane. The first principal plane of the implant at the implant plane is denoted as FP, The second principal plane of the implant at the implant plane is denoted as SP. In both scenarios, the vergence should be the same before vitreous chamber (i. e. at SP plane). By equating the vergence calculated from two difference scenarios, the relationship can be found to decide the desired implant power at implant plane. More specifically, the desired implant at implant plane will be a function of the vergence immediately after the cornea ($L_{Cornea}$), the desired implant power at the corneal plane ($P_{Implant}'$), the distance between the second principal plane of the cornea (close to the anterior corneal surface) and the first principal plane of the implant (d) and refractive index of aqueous (n). In the discussion of toric value calculation, d and n can be fixed as constants.

$$P_{IOL}=f(L_{cornea}, P_{Implant}', d, n)=f_{d,n}(L_{cornea}, P_{Implant}') \quad (6)$$

From the first optical system, the vergence at the SP plane is:

$$L'_{Implant} = \frac{L_{cornea}}{1 - \frac{d}{n} L_{cornea}} + P_{Implant} \quad (7)$$

From the second virtual optical setup, considering the location shift of implant, the vergence at the SP plane is:

$$L'_{Implant} = \frac{P'_{Implant} + L_{cornea}}{1 - \frac{d}{n}(P'_{Implant} + L_{cornea})} \quad (8)$$

By equating the right sides of equation (7) and (8), $$\frac{L_{cornea}}{1 - \frac{d}{n} L_{cornea}} + P_{Implant} = \frac{P'_{Implant} + L_{cornea}}{1 - \frac{d}{n}(P'_{Implant} + L_{cornea})} \quad (9)$$

the following is obtained:

$$P'_{Implant} = \frac{P_{Implant}\left(1 - \frac{d}{n} L_{cornea}\right)^2}{1 + \frac{d}{n} P_{Implant}\left(1 - \frac{d}{n} L_{cornea}\right)} \quad (10)$$

$$P_{Implant} = \frac{P'_{Implant}}{\left(1 - \frac{d}{n} L_{cornea}\right)\left(1 - \frac{d}{n}(P'_{Implant} + L_{cornea})\right)} \quad (11)$$

The equation (10) calculates the equivalent implant at the corneal plane for a given implant at the implant plane. The equation (11) computes the desired implant power at the implant plane according to the required optical power at corneal plane. The desired toric value can be obtained by taking the difference between maximum and minimum powers.

Assuming that the optical axial length is $AL_O$, the required implant power at the corneal plane can be calculated as $$P'_{Implant} = \frac{N}{AL_O} - L_{cornea} \quad (12)$$

For example, patient has k-reading K1=42.75 D×120°, K2=44.75 D×30°. Assume that there's no induced astigmatism by surgeon, the emmetropic eye has axial length 23.65 mm, d=5.20 mm and n=1.336. The required implant powers at the corneal plane are 13.74 D×120°and 11.74 D×30°. Putting these values into equation (11), the implant powers at implant plane are 21.13 D×120°and 18.22×30°. Compared the toric value of the cornea 2.00 D, the implant should have toric value −2.91 D, which gives a conversion factor of 1.46.

Equation (11) includes both $L_{cornea}$ and $P_{Implant}'$, therefore, it must be determined which variable affect the calculation of spherical and cylindrical powers most and could the effects of these two factors on toric values be constant by differentiating the equation (11).

$$dP_{Implant} = \frac{\partial P_{Implant}}{\partial P'_{Implant}} dP'_{Implant} + \frac{\partial P_{Implant}}{\partial L_{cornea}} dL_{cornea} \quad (13)$$

$$Cyl_{Implant} = \frac{\partial P_{Implant}}{\partial P'_{Implant}} Cyl'_{Implant} + \frac{\partial P_{Implant}}{\partial L_{cornea}} Cyl_{cornea} \quad (14)$$

$$C_1 = \frac{\partial P_{Implant}}{\partial P'_{Implant}}, \; C_2 = \frac{\partial P_{Implant}}{\partial L_{cornea}} \quad (15)$$

where $dP_{Implant}$ can be considered as the change of spherical power due to choosing different meridians and therefore can be treated as the cylindrical power of the implant, similarly, the $dP_{Implant}'$ can be treated as the cylindrical power of the implant at the corneal plane, the $dL_{cornea}$ as the cylindrical power of the cornea. Intuitively, the equation (14) means that the cylindrical power of the implant is a function of its power at the corneal plane and the cylindrical power of the cornea, which is shown by equation (15). If the coefficients before $dP_{Implant}'$ ($Cyl_{Implant}'$) and $dL_{cornea}$ ($Cyl_{cornea}$), $$\frac{\partial P_{Implant}}{\partial P'_{Iμμπλαν}} \text{ and} \quad (16)$$

$$\frac{\partial P_{Implant}}{\partial L_{cornea}} \quad (17)$$

are constants, the equation (14) would be a linear equation. However, these two coefficients are usually not constants, but the functions of $P_{Implant}'$ and $L_{cornea}$.

With additional calculations, it can be determined that $$C_1 = \frac{\partial P_{Implant}}{\partial P'_{Implant}} = \frac{1}{\left(1 - \frac{d}{n}(P'_{Implant} + L_{cornea})\right)^2} \quad (18)$$

$$C_2 = \frac{\partial P_{Implant}}{\partial L_{cornea}} \quad (19)$$
$$= \frac{1}{\left(1 - \frac{d}{n}(P'_{Implant} + L_{cornea})\right)^2} - \frac{1}{\left(1 - \frac{d}{n} L_{cornea}\right)^2}$$

In equation (15), the desired IOL cylinder value ($Cyl_{IOL}'$) at corneal plane is equal to $C_{Xcyl}$, and the corneal cylinder ($Cyl_{cornea}$, including surgical induced astigmatism) is equal to the refractive error to be corrected, $-C_{Xcyl}$.

Therefore, the equation (15) can be rewritten as:

$$Cyl_{Implant} = (C_1 - C_2) \cdot C_{Xcyl} = CF \cdot C_{Xcyl} \quad (20)$$

The $CF=C_1-C_2$ is highly dependent on d and corneal K values. For corneal powers within the normal range of 35 D-55 D, the conversion factor (CF) can be calculated with equation (18) and (19) by fixing d to be the mean value of each region of interest.

For 0 mm≦d<0.25 mm, CF=1.00;
for 0.25 mm≦d<0.75 mm, CF=1.02-1.04;
for 0.75 mm≦d<1.25 mm, CF=1.05-1.09;
for 1.25 mm≦d<1.75 mm, CF=1.08-1.14;
for 1.75 mm≦d<2.25 mm, CF=1.11-1.19;
for 2.25 mm≦d<2.75 mm, CF=1.15-1.24;
for 2.75 mm≦d<3.25 mm, CF=1.18-1.30;

for 3.25 mm$\leq$d<3.75 mm, CF=1.21-1.37;
for 3.75 mm$\leq$d<4.25 mm, CF=1.25-1.43;
for 4.25 mm$\leq$d<4.75 mm, CF=1.29-1.51;
for 4.75 mm$\leq$d$\leq$5.25 mm, CF=1.32-1.59;
for 5.25 mm<d$\leq$5.75 mm, CF=1.37-1.67;
for 5.75 mm<d$\leq$6.25 mm, CF=1.41-1.76;
for 6.25 mm<d$\leq$6.75 mm, CF=1.45-1.86;
for 6.75 mm<d$\leq$7.25 mm, CF=1.50-1.97.

For implants, such as refractive implants, that are to be located near or in the cornea, power transfer step 20 is not necessary. Once the required power of the implant is determined at step 18 and/or step 20, this calculated power can be used to select the appropriate lens model and report the lens model to the operator in steps 22 and 24, respectively. The lens power calculation and axial placement may also be reported to the operator in steps 26 and 28, respectively. The present invention therefore, provides an accurate method for calculating the required power of a toric implant by using both the measured pre-operative corneal/ocular astigmatism and the predicted surgically-induced astigmatism.

This description is given for purposes of illustration and explanation. It will be apparent to those skilled in the relevant art that changes and modifications may be made to the invention described above without departing from its scope or spirit.

We claim:

1. A method of selecting an ophthalmic lens implant at a corneal plane and at an implant plane, comprising the steps of:
   a) determining the spherical and cylindrical powers of an optical system of a human eye;
   b) equating two equivalent optical systems when the implant is at the corneal plane and when the implant is at the implant plane;
   c) calculating a spherical power of the ophthalmic lens implant at the corneal plane and at the implant plane based upon the results of steps (a) and (b);
   d) calculating a toric power of the implant at the corneal plane and at the implant plane by using a dioptric difference of spherical powers between steep and flat meridians; and
   e) selecting the ophthalmic lens implant based on the calculated spherical power and the calculated toric power.

2. The method of claim 1 wherein the determined spherical and cylindrical powers of the optical system of the human eye includes surgically-induced astigmatism.

3. The method of claim 2 wherein the surgically-induced astigmatism is included using vector analysis.

* * * * *